(12) United States Patent
Beck

(10) Patent No.: US 6,477,411 B1
(45) Date of Patent: Nov. 5, 2002

(54) BIOELECTRODE HAVING A CRUSHABLE HYDRATING ASSEMBLY AND ASSOCIATED METHOD

(75) Inventor: Jon E. Beck, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 50 days.

(21) Appl. No.: 09/587,006

(22) Filed: Jun. 5, 2000

(51) Int. Cl.⁷ .................................................. A61N 1/30
(52) U.S. Cl. ........................ 604/20; 607/152; 607/153; 401/132; 401/133; 606/215
(58) Field of Search ........................... 604/20; 606/215; 600/272–273, 393, 395; 607/152, 153; 401/132, 133

(56) References Cited

U.S. PATENT DOCUMENTS

| | | | |
|---|---|---|---|
| 3,466,131 A | * | 9/1969 | Arcudi ........................ 401/132 |
| 3,768,916 A | * | 10/1973 | Avery ......................... 401/132 |
| 4,183,684 A | * | 1/1980 | Avery, Jr. .................... 401/132 |
| 4,784,506 A | * | 11/1988 | Koreska et al. ............. 401/132 |
| 5,288,289 A | | 2/1994 | Haak et al. .................. 604/20 |
| 5,310,404 A | | 5/1994 | Gyory et al. ................. 604/20 |
| 5,336,219 A | | 8/1994 | Krantz ......................... 606/15 |
| 5,383,900 A | | 1/1995 | Kranz ......................... 606/215 |
| 5,445,462 A | | 8/1995 | Johnson et al. ............... 604/3 |
| 5,538,353 A | * | 7/1996 | DeHavilland ............... 401/132 |
| 5,645,527 A | | 7/1997 | Beck ........................... 604/20 |
| 5,690,958 A | | 11/1997 | McGrath ..................... 424/451 |
| 5,730,716 A | | 3/1998 | Beck et al. .................. 604/20 |
| 5,772,346 A | | 6/1998 | Edwards ....................... 604/3 |
| 5,947,920 A | * | 9/1999 | Beck ........................... 604/20 |

FOREIGN PATENT DOCUMENTS

| | | | |
|---|---|---|---|
| EP | 0 082 728 | 6/1983 | |
| WO | WO 93/24177 | 12/1993 | ................. 604/20 |

* cited by examiner

*Primary Examiner*—Thomas Denion
*Assistant Examiner*—Thai-Ba Trieu
(74) *Attorney, Agent, or Firm*—Factor & Partners (57) ABSTRACT

A hydratable bioelectrode for use in an iontophoretic delivery device comprising a hydrating component and a bioelectrode component. The hydrating component includes a cradle having a chamber containing one or more fluid containing ampule(s) and ampule breaking means associated with the cradle for rapidly breaking the one or more fluid containing ampule(s).

29 Claims, 6 Drawing Sheets

BIOELECTRODE HAVING A CRUSHABLE HYDRATING ASSEMBLY AND ASSOCIATED METHOD

BACKGROUND OF THE INVENTION

1. Field of the Invention

The present invention relates in general to iontophoretic delivery devices used to deliver ionic medicaments through the skin or other tissues, and more particularly, to crushable hydration assemblies for hydrating a bioelectrode element of an iontophoretic delivery device.

2. Background Art

Iontophoretic delivery devices have been known in the art for several years. Furthermore, iontophoretic delivery devices having hydration assemblies for hydrating bioelectrodes are likewise well known and are the subject of many U.S. Patents including: PCT Application No. WO/93/24177; PCT Application No. WO/92/07619; U.S. Pat. No. 5,730,716; and U.S. Pat. No. 5,645,527.

PCT Application No. WO/93/24177 discloses an iontophoretic delivery device which includes drug and electrolyte matrix pads that are initially unfilled, in a non-hydrated state. A sealed liquid-containing capsule or pouch is provided in each electrode assembly. Water or other liquid is released from the pouch by pulling a tab attached to a portion of the pouch which is capable of being torn or ripped in order to hydrate the drug and electrolyte reservoirs. The '177 application further discloses a device which includes liquid storage pouches which move through a compression zone when removing the device from an outer package. The compression forces a puncturing device to break into the pouches and in turn, releases the associated liquid.

PCT Application No. WO/92/07619 discloses an iontophoretic drug delivery electrode and method of hydrating the same. In particular, the device includes drug and electrolyte matrix pads which are initially in a non-hydrated state. Liquid can be contained in breakable capsules within a pouch. The capsules are broken by directly squeezing or flexing the pouches. The '619 application further discloses an iontophoretic drug delivery device wherein fluid is released from a pouch using piercing pins.

U.S. Pat. No. 5,730,716 discloses an iontophoretic delivery device which includes a "pouch" like hydration assembly that, upon displacement of a pull tab, unfolds, thereby releasing medicament and/or an electrolyte solution therefrom.

U.S. Pat. No. 5,645,527 discloses a hydration assembly for hydrating a bioelectrode, wherein the hydration assembly can be activated by a user through application of force to a pocket in a side of a sealed-liquid storage component to cause the pocket to become inverted and substantially align with an opposing pocket in the other side such that the sealed liquid-storage compartment unseals at a predetermined release location.

SUMMARY OF THE INVENTION

The present invention is directed to a hydratable bioelectrode for use in an iontophoretic delivery device comprising: (a) a hydrating component, wherein the hydrating component includes: (1) a cradle having a chamber capable of retaining one or more fluid containing ampules and (2) at least one displaceable flange associated with the cradle which is capable of breakably engaging one or more fluid containing ampules retained within the chamber upon application of an applied force; and (b) a bioelectrode component associated with the hydrating component.

In a preferred embodiment of the invention, the at least one displaceable flange comprises a pair of substantially parallel inwardly depressable flanges.

Preferably the cradle further comprises one or more ampule engaging tabs positioned on an inner surface of the same.

In another preferred embodiment of the invention, the hydratable bioelectrode further comprises means for substantially precluding ampule breakage from contacting the bioelectrode component. In this embodiment the ampule breakage contacting preclusion means may include a mesh, scrim, or screen guard positioned between the hydrating component and the bioelectrode component.

In yet another preferred embodiment of the present invention, the bioelectrode component is slidably, snapidly, hingedly, adhesively, or otherwise fixiated mounted to a chassis member of an iontophoretic delivery device. The present invention is also directed to an iontophoretic delivery device, comprising: (a) a cradle having a chamber containing one or more fluid containing ampules; (b) ampule breaking means associated with the cradle for rapidly breaking the one or more fluid containing ampules; and (c) a bioelectrode component associated with the hydrating component.

The present invention is further directed to a process for hydrating a hydratable bioelectrode, comprising the steps of: (a) providing a hydrating component including a cradle having a chamber filled with one or more fluid containing ampules and at least one displaceable flange associated with the cradle; (b) providing a bioelectrode component; (c) displacing the at least one displaceable flange with an applied force; (d) breaking the one or more fluid containing ampules with the displaced flange; and (e) releasing the fluid from the one or more ampules onto the bioelectrode component.

Preferably the step of displacing the at least one displaceable flange with an applied force includes the step of inwardly depressing the same.

BRIEF DESCRIPTION OF THE DRAWINGS

The invention will now be described with reference to the drawings wherein.

DETAILED DESCRIPTION OF THE INVENTION

While this invention is susceptible of embodiment in many different forms, there is shown in the drawings and described herein in detail several specific embodiments with the understanding that the present disclosure is to be considered as an exemplification of the principles of the invention and is not intended to limit the invention to the embodiments illustrated.

Figure 1:
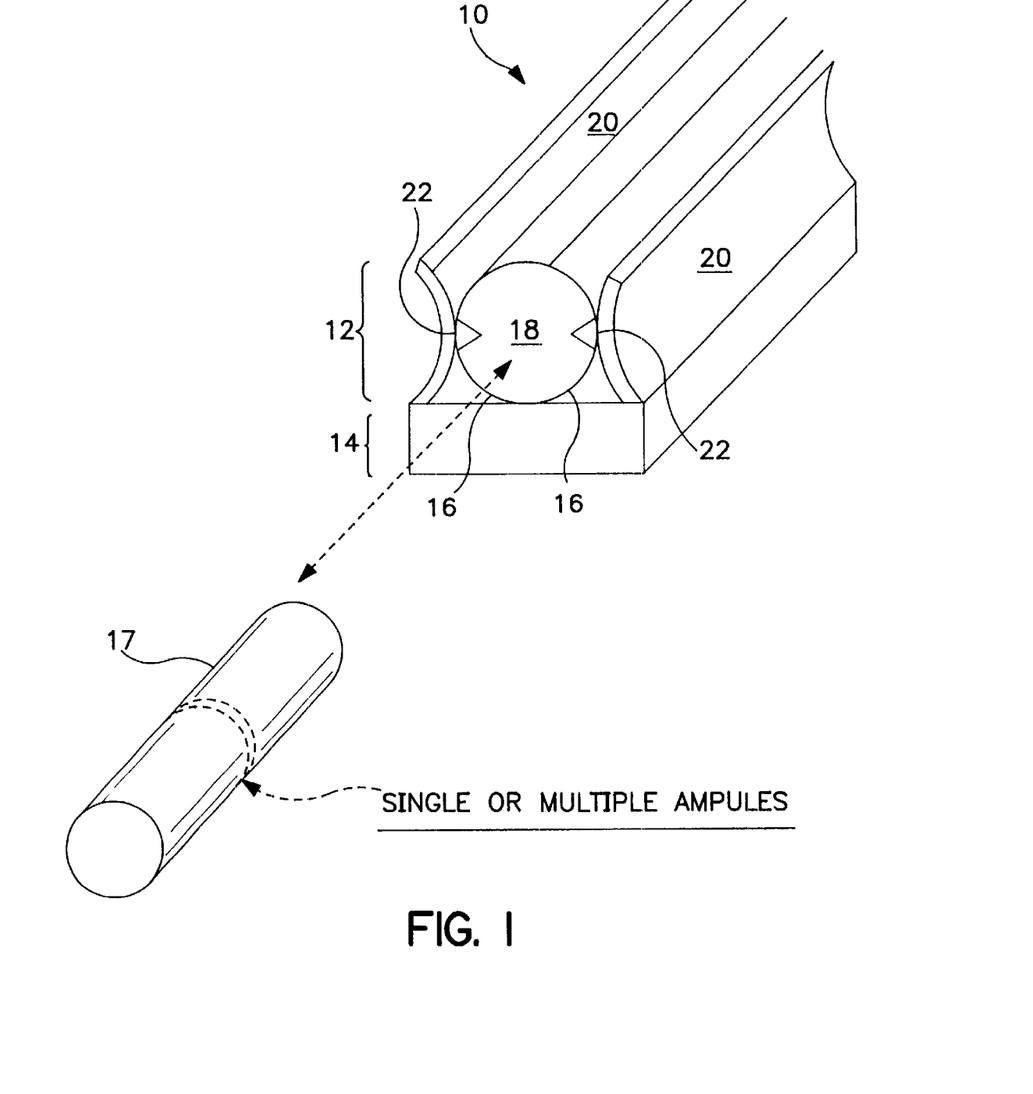
FIG. 1 of the drawings is a perspective view of a bioelectrode in accordance with the present invention.

Referring now to the drawings and to FIG. 1 in particular, a first embodiment of a hydratable bioelectrode 10 is shown, which generally comprises hydrating component 12 and bioelectrode 14.

Figure 2A:
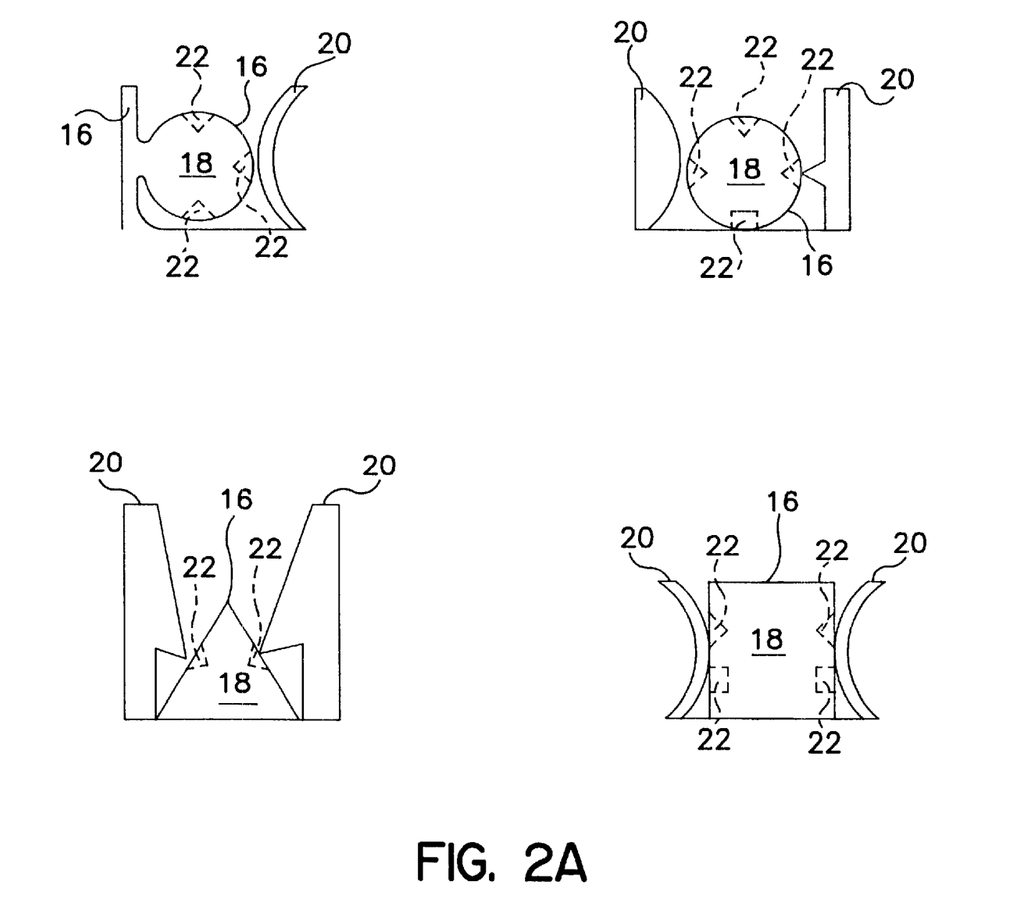
FIG. 2A of the drawings is a fragmented cross-sectional view of hydrating components in accordance with the present invention showing, among other things, the geometric configuration of associated cradles and flanges.
Figure 2B:
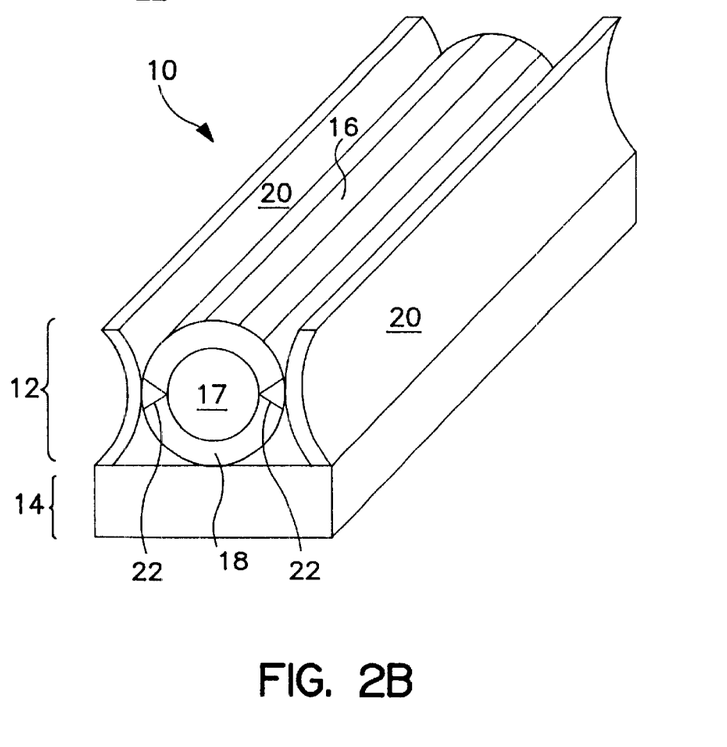
FIG. 2B of the drawings is a fragmented cross-sectional view of hydrating components in accordance with the present invention showing, among other things, the geometric configuration of associated flanges.

Hydrating component 12 includes cradle 16 having chamber 18 which is capable of retaining one or more fluid containing ampule(s) 17. Ampule(s) 17 may contain, for example, an ionic medicament, and/or an electrolyte solution. For example, as is shown in FIG. 2B, a single ampule 17 can be associated with a single bioelectrode 14 if the ionic medicament and the electrolyte solution can be mixed prior to application of the same. Alternatively, as is also shown in FIG. 2B, first and second ampules 17 can be associated with separate bioelectrodes 14 when the ionic medicament and electrolyte solution are not compatible with single ampule applications. A pair of flanges 20 are associated with cradle 16, which are capable of breakably engaging ampule(s) retained within chamber 18 upon application of an applied force.

Cradle 16 is preferably configured to substantially conform to the outer peripheral geometry of associated ampule(s). However, as is shown in FIG. 2A, any one of a number of geometric configurations are contemplated for use—so long as the configuration enables breakage of associated ampule(s) upon application of an applied force. As is further shown in FIG. 2A, the inner surface of cradle 16 can be associated with tabs 22. Tabs 22 can serve to, among other things, provide pressure points for directing breakage of the ampule(s) at a particular location if desired.

For purposes of the present disclosure, a pair of substantially parallel, inwardly depressable flanges 20 are associated with cradle 16. However, as is shown in FIGS. 2A and 2B, it will be understood that numerous other flange configurations are suitable for use in accordance with the present invention. For example, as is shown in FIG. 2A, flanges 20 include at least one arcuate surface to assist in providing a concentrated pressure point upon application of an applied force.

Cradle 16 and flanges 20 can be fabricated from any one of a number of materials including, for example, natural and synthetic plastic resins, metals, metal alloys, etc.

Figure 3:
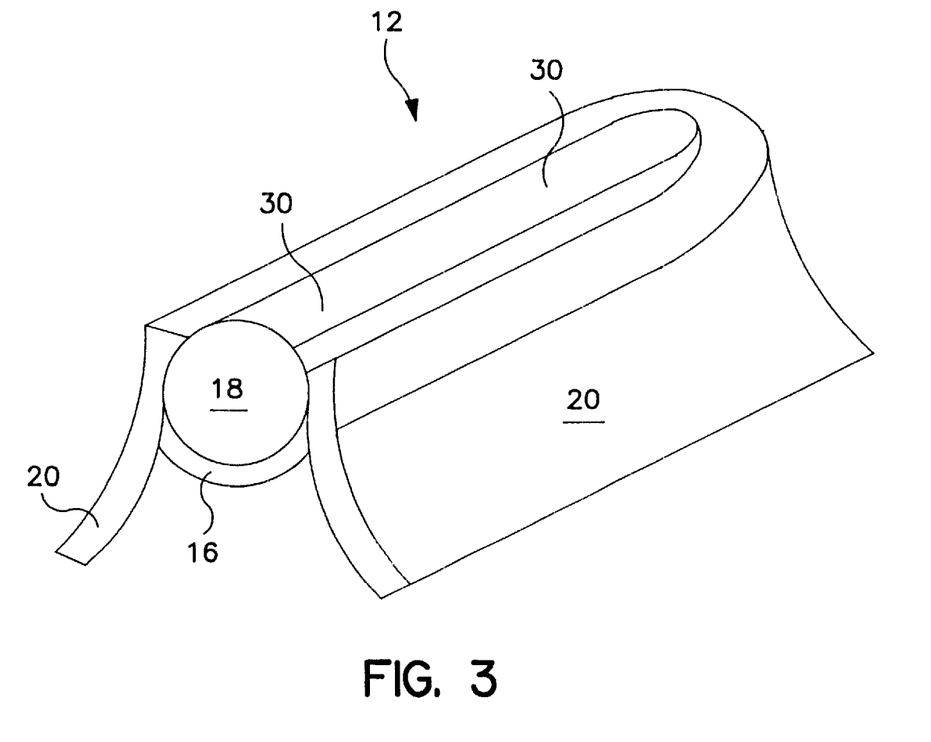
FIG. 3 of the drawings is a perspective view of a bioelectrode in accordance with the present invention showing, among other things, a mesh or screen guard associated with a hydrating component in accordance with the present invention.

As is shown in FIG. 3, hydrating component 12 can be associated with means for substantially precluding any ampule breakage from contacting bioelectrode element 14. In particular, a mesh or screen guard 30 can be positioned between hydrating element 12 and bioelectrode element 14. While the ampule breakage contacting preclusion means has been disclosed as being fabricated from a mesh or screen material, it will be understood that other materials that would be known to those having ordinary skill with the present disclosure before them are likewise contemplated for use. For Example, it is contemplated that any material which would allow liquids to pass through such gauze, a nonwoven scrim or tricot weave, etc., can be used or a defined route of liquid leakage or diffusion (tube, holes, etc.).

Figure 4:
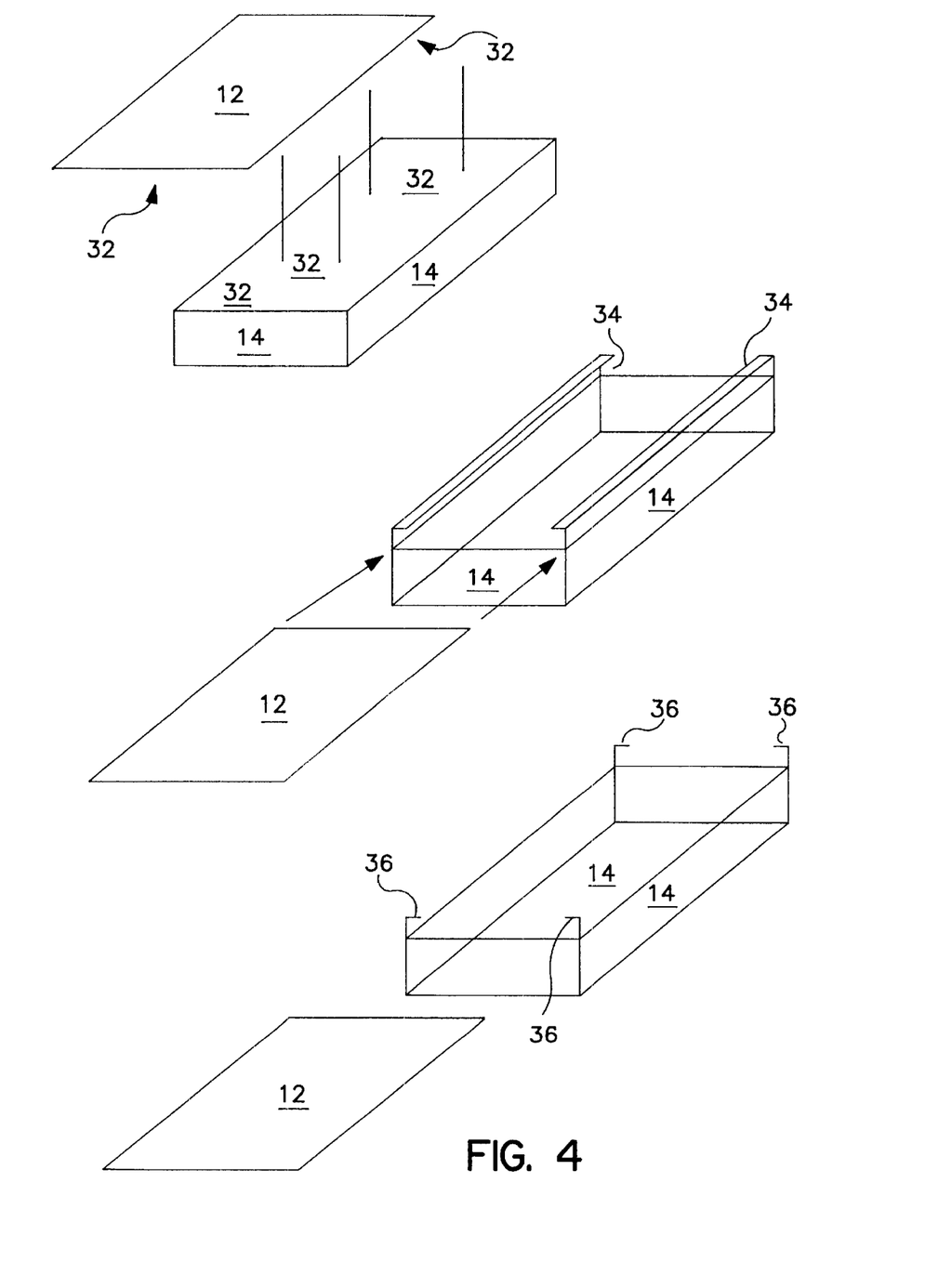
FIG. 4 of the drawings is a perspective view of a bioelectrode in accordance with the present invention showing, among other things, mounting mechanisms in accordance with the present invention.

For purposes of the present disclosure, bioelectrode 14 comprises conventional materials well known in the art including, for example, those disclosed in U.S. Pat. No. 5,730,716, and U.S. Pat. No. 5,645,527, which are hereby incorporated by reference in their entirety. As is shown in FIG. 4, bioelectrode 14 can be associated with hydrating component 12 using numerous mechanisms including adhesives 32 as well as sliding and clipping mechanisms, 34 and 36, respectively.

Hydrating component 12 and bioelectrode component 14 of bioelectrode 10 can be mounted to a chassis member of an iontophoretic delivery device as is disclosed in the above-referenced '716 patent. In particular, bioelectrode 12 can be, for example, adhesively or slidably mounted in an optionally releasable manner similar to the configurations disclosed in FIG. 4. It is also contemplated that other communication mounting methods be used, including, but not limited weldings used at a hinge, screws/fasteners, etc.

In operation, hydrating the hydratable bioelectrode is initiated upon providing a hydrating component including a cradle having a chamber filled with one or more fluid containing ampules and at least one displaceable flange associated with the chamber, and a bioelectrode component. Next, the at least one displaceable flange is displaced by application of an applied force, such as by a user inwardly depressing the same. The application of the applied force breaks the one or more fluid containing ampules, thereby releasing the fluid from the one or more ampules onto the bioelectrode component.

Figure 5:
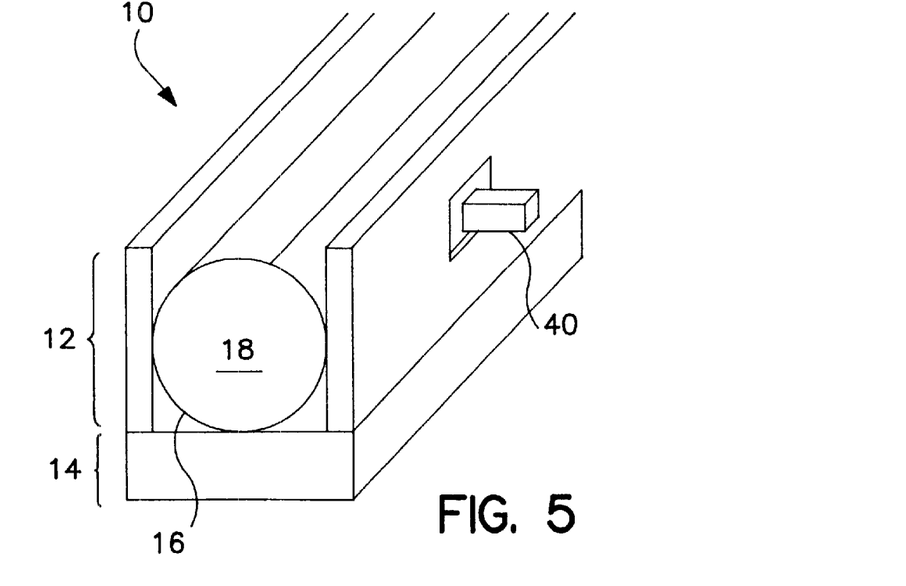
FIG. 5 of the drawings is a perspective view of a bioelectrode in accordance with the present invention showing, among other things, ampule breaking means comprising a slidable push pin/peg mechanism in accordance with the present invention.

Referring now to the drawings and to FIG. 5 in particular, a second embodiment of a hydratable bioelectrode 10 is shown, which generally comprises hydrating component 12 and bioelectrode 14.

Figure 6:
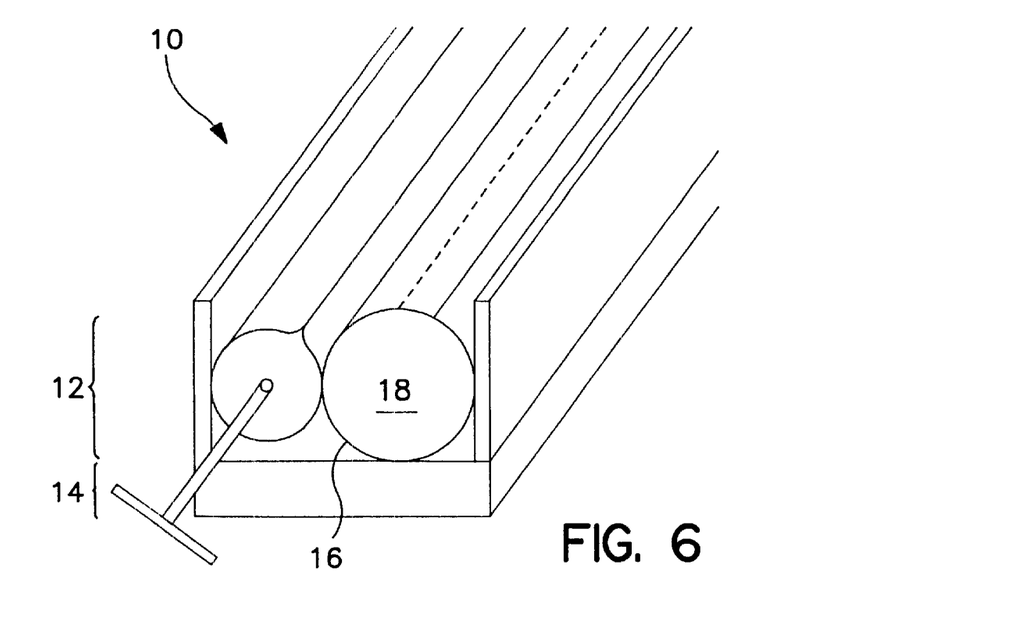
FIG. 6 of the drawings is a perspective view of a bioelectrode in accordance with the present invention showing, among other things, ampule breaking means comprising a twist key/cam rotary actuated mechanism in accordance with the present invention.

Hydrating component 12 includes cradle 16 having chamber 18 which is capable of retaining one or more fluid containing ampule(s) 17. Ampule breaking means 40 are associated with cradle 16, which are capable of breakably engaging ampule(s) retained within chamber 18 upon application of an applied force. In particular, ampule breaking means 40 may include, for example, a slidable push pin/peg mechanism which ruptures ampule(s) 17 upon inward actuation of the same. Alternatively, and as is shown in FIG. 6, ampule breaking means 40 may include a twist key/cam mechanism which ruptures ampule(s) 17 upon rotary actuation of the same. While the above-provided ampule breaking means have been disclosed, for illustrative purposes only, it will be understood that other mechanisms for breaking associated ampule(s) are likewise contemplated for use including mechanisms that hinge, slide, roll, twist, cam, or otherwise deflect to cause one or more associated ampule(s) to be crushed, cracked, or otherwise altered from their original pre-manipulated state.

While specific embodiments have been disclosed, for illustrative purposes only, it will be understood that the hydratable bioelectrode may be incorporated into numerous iontophoretic drug delivery devices either as single dose disposable units or integrated replaceable units—as are disclosed in the previously references and incorporated '716 and '527 patents.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A hydratable bioelectrode for use in an iontophoretic delivery device, comprising:
    a hydrating component, wherein the hydrating component includes:
        a cradle having a chamber capable of retaining one or more fluid containing ampules;
        at least one displaceable flange associated with the cradle which is capable of breakably engaging one or more fluid containing ampules retained within the chamber upon application of an applied force; and
    a bioelectrode component associated with the hydrating component.

2. The hydratable bioelectrode according to claim 1, wherein the at least one displaceable flange comprises a pair of displaceable flanges.

3. The hydratable bioelectrode according to claim 1, wherein the at least one displaceable flange comprises a pair of substantially parallel displaceable flanges.

4. The hydratable bioelectrode according to claim 1, wherein the at least one displaceable flange comprises a pair of substantially parallel inwardly depressable flanges.

5. The hydratable bioelectrode according to claim 4, wherein the pair of substantially parallel inwardly depressable flanges each comprise an outer surface and an inner surface, wherein at least one of the inner and outer surfaces of each flange is arcuate.

6. The hydratable bioelectrode according to claim 5, wherein the cradle further comprises one or more ampule engaging tabs positioned on an inner surface of the same.

7. The hydratable bioelectrode according to claim 1, wherein the cradle further comprises one or more ampule engaging tabs positioned on an inner surface of the same.

8. The hydratable bioelectrode according to claim 1, further comprising means for substantially precluding ampule breakage from contacting the bioelectrode component.

9. The hydratable bioelectrode according to claim 8, wherein the ampule breakage contacting preclusion means comprises a mesh or screen guard positioned between the hydrating component and the bioelectrode component.

10. The hydratable bioelectrode according to claim 1, wherein the bioelectrode component is mounted to a chassis member of an iontophoretic delivery device.

11. The hydratable bioelectrode according to claim 10, wherein the bioelectrode is adhesively mounted to the chassis member of an iontophoretic delivery device.

12. The hydratable bioelectrode according to claim 10, wherein the bioelectrode is slidably mounted to the chassis member of an iontophoretic delivery device.

13. A hydratable bioelectrode for use in an iontophoretic delivery device, comprising:
    a cradle having a chamber containing one or more fluid containing ampules;
    ampule breaking means associated with the cradle for rapidly breaking the one or more fluid containing ampules; and
    a bioelectrode component associated with the hydrating component.

14. The hydratable bioelectrode according to claim 13, wherein the ampule breaking means comprises a pair of displaceable flanges.

15. The hydratable bioelectrode according to claim 13, wherein the ampule breaking means comprises a pair of substantially parallel displaceable flanges.

16. The hydratable bioelectrode according to claim 13, wherein the ampule breaking means comprises a pair of substantially parallel inwardly depressable flanges.

17. The hydratable bioelectrode according to claim 13, further comprising means for substantially precluding ampule breakage from contacting the bioelectrode component.

18. The hydratable bioelectrode according to claim 17, wherein the ampule breakage contacting preclusion means comprises a mesh or screen guard positioned between the hydrating component and the bioelectrode component.

19. The hydratable bioelectrode according to claim 13, wherein the ampule breaking means comprises a slidable push pin/peg mechanism.

20. The hydratable bioelectrode according to claim 13, wherein the ampule breaking means comprises a twist key/cam mechanism.

21. The hydratable bioelectrode according to claim 13, wherein the ampule breaking means comprises at least one mechanism selected from the group consisting of a hinge, slide, roll, twist, or cam mechanism.

22. The hydratable bioelectrode according to claim 13, wherein the bioelectrode component is mounted to a chassis member of an iontophoretic delivery device.

23. The hydratable bioelectrode according to claim 22, wherein the bioelectrode is adhesively mounted to the chassis member of an iontophoretic delivery device.

24. The hydratable bioelectrode according to claim 22, wherein the bioelectrode is slidably mounted to the chassis member of an iontophoretic delivery device.

25. A hydratable bioelectrode for use in an iontophoretic delivery device, comprising:
    a hydrating component, wherein the hydrating component includes:

a cradle having a chamber containing one or more fluid containing ampules;

a pair of substantially parallel inwardly depressable flanges which are capable of breakably engaging the one or more fluid containing ampules retained within the chamber upon application of an applied force; and a bioelectrode component associated with the hydrating component.

26. The hydratable bioelectrode according to claim 25, further comprising means for substantially precluding ampule breakage from contacting the bioelectrode component.

27. The hydratable bioelectrode according to claim 26, wherein the ampule breakage contacting preclusion means comprises a mesh or screen guard positioned between the hydrating component and the bioelectrode component.

28. A process for hydrating a hydratable bioelectrode, comprising the steps of:

providing a hydrating component including a cradle having a chamber filled with one or more fluid containing ampules and at least one displaceable flange associated with the chamber;

providing a bioelectrode component;

displacing the at least one displaceable flange with an applied force;

breaking the one or more fluid containing ampules with the displaced flange; and releasing the fluid from the one or more ampules onto the bioelectrode component.

29. The process according to claim 28, wherein the step of displacing the at least one displaceable flange with an applied force includes the step of inwardly depressing the same.

* * * * *